United States Patent
Oguri et al.

(10) Patent No.: US 9,715,999 B2
(45) Date of Patent: Jul. 25, 2017

(54) CHROMATOGRAPH MASS SPECTROMETER

(71) Applicant: SHIMADZU CORPORATION, Kyoto-shi, Kyoto (JP)

(72) Inventors: Masateru Oguri, Takatsuki (JP); Manabu Ueda, Kyotanabe (JP)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 0 days.

(21) Appl. No.: 15/031,160

(22) PCT Filed: Oct. 22, 2013

(86) PCT No.: PCT/JP2013/078515
§ 371 (c)(1),
(2) Date: Apr. 21, 2016

(87) PCT Pub. No.: WO2015/059760
PCT Pub. Date: Apr. 30, 2015

(65) Prior Publication Data
US 2016/0240358 A1    Aug. 18, 2016

(51) Int. Cl.
*H01J 49/00* (2006.01)
*G01N 30/72* (2006.01)

(52) U.S. Cl.
CPC ............ *H01J 49/005* (2013.01); *G01N 30/72* (2013.01); *H01J 49/0031* (2013.01)

(58) Field of Classification Search
CPC ...... H01J 49/00; H01J 49/0045; H01J 49/005; H01J 49/0054; H01J 49/0059; H01J 49/0072; H01J 49/02
(Continued)

(56) References Cited

U.S. PATENT DOCUMENTS

| 2005/0098719 A1* | 5/2005 | Thomson | H01J 49/0081 250/288 |
| 2007/0138384 A1* | 6/2007 | Keiser | H01J 49/0031 250/282 |
| 2013/0221233 A1* | 8/2013 | Whitehouse | H01J 49/147 250/396 R |

FOREIGN PATENT DOCUMENTS

JP    2012-104389 A    5/2012

OTHER PUBLICATIONS

Written Opinion for PCT/JP2013/078515 dated Dec. 3, 2013. [PCT/ISA/237].
(Continued)

*Primary Examiner* — Jason McCormack
(74) *Attorney, Agent, or Firm* — Sughrue Mion, PLLC (57) ABSTRACT

A chromatograph mass spectrometer including an optimum gas pressure search controller that performs an MRM measurement for a target compound while changing a collision-gas pressure, investigates an optimum collision-gas pressure giving a highest signal strength based on the measured result, and stores the same gas pressure for each compound in a compound-related information storage section. When a target compound is specified in a simultaneous multicomponent analysis, a control sequence determiner reads the optimum collision-gas pressure and retention time information corresponding to the specified compound from the storage section, prepares a control sequence which sets the gas pressure in a collision cell at the optimum gas pressure at the timing where each compound is eluted, and stores the sequence in a control sequence storage section.

12 Claims, 6 Drawing Sheets

(58) Field of Classification Search
USPC .................. 250/281, 282, 283, 284, 288
See application file for complete search history.

(56) References Cited

OTHER PUBLICATIONS

Communication dated Oct. 7, 2016 from the European Patent Office in counterpart application No. 13895843.4.
M. Judith Charles et al., "Collision Energy, Collision Gas, and Collision Gas Pressure Effects on the Formation of 2,3,7,8-Tetrachlorodibenzo-p-dioxin and 2,3,7,8-Tetrabronnodibenzo-p-dioxin Product Ions," Anal. Chem., vol. 63, No. 7, Apr. 1, 1991, pp. 713-721.
International Search Report for PCT/JP2013/078515 dated Dec. 3, 2013 [PCT/ISA/210].

* cited by examiner

FLOW INJECTION METHOD

Fig. 2B

COLLISION-GAS PRESSURE AND SIGNAL STRENGTH

Fig. 3A

INFUSION METHOD

Fig. 3B

COLLISION-GAS PRESSURE AND SIGNAL STRENGTH

CHROMATOGRAPH MASS SPECTROMETER

CROSS REFERENCE TO RELATED APPLICATIONS

This application is a National Stage of International Application No. PCT/JP2013/078515, filed on Oct. 22, 2013, the contents of all of which are incorporated herein by reference in their entirety.

TECHNICAL FIELD

The present invention relates to a chromatograph mass spectrometer including a chromatograph (such as a liquid chromatograph or gas chromatograph) combined with a mass spectrometer. More specifically, it relates to a chromatograph mass spectrometer in which a mass spectrometer capable of performing an MS/MS analysis utilizing the collision-induced dissociation is used as the mass spectrometer.

BACKGROUND ART

An MS/MS analysis (also called the "tandem analysis"), which is one of the mass spectrometric techniques, has been widely used in recent years, mainly for the purpose of identifying substances having high molecular weights and analyzing their structures. A triple quadrupole mass spectrometer (also called the "tandem quadrupole mass spectrometer" or otherwise) is one type of mass spectrometer capable of MS/MS analyses and is popularly used since it has a comparatively simple structure and is inexpensive.

A triple quadrupole mass spectrometer normally has a collision cell for dissociating an ion by collision-induced dissociation, which is placed between the two quadrupole mass filters provided on the front and rear sides of the cell, respectively. The front quadrupole mass filter selects a precursor ion having a specific mass-to-charge ratio from among various ions derived from a target compound, while the rear quadrupole mass filter separates various product ions produced from the precursor ion according to their mass-to-charge ratios. The collision cell is a box-like structure which is hermetically sealed to a comparatively high degree, into which an inert gas (such as argon or nitrogen) is introduced as the collision gas. The precursor ion selected by the front quadrupole mass filter is given an appropriate amount of collision energy and introduced into the collision cell. Within this collision cell, the ion collides with the collision gas and undergoes the collision-induced dissociation process, whereby the product ions are produced.

The dissociation efficiency of the ion within the collision cell depends on the amount of collision energy possessed by the ion introduced into the collision cell, the pressure of the collision gas in the collision cell (hereinafter, the term "collision-gas pressure" should mean "the pressure of the collision gas in the collision cell" unless otherwise noted), and other factors. Therefore, the detection sensitivity of the product ions also depends on the amount of collision energy and the collision-gas pressure. Additionally, even when the collision-gas pressure is the same, the dissociation efficiency of the ion varies depending on the kind of compound (or to be exact, the kind of precursor ion). Therefore, when a multiple reaction monitoring (MRM) measurement mode for selectively detecting a product ion having a specific mass-to-charge ratio generated from a precursor ion having a specific mass-to-charge ratio is performed in order to determine the quantity of a compound, the analysis operator sets the collision-gas pressure at an optimum level at which the detection sensitivity to the product ion originating from the target compound will be at its highest level.

In recent years, a liquid chromatograph mass spectrometer (LCMS) or gas chromatograph mass spectrometer (GC/MS) in which a liquid chromatograph (LC) or gas chromatogram (GC) is combined with a mass spectrometer has been often used to perform a simultaneous multicomponent analysis for a sample containing a number of compounds (see Patent Literature 1). When a simultaneous multicomponent analysis by an MRM measurement is conducted in an LC/MS or GC/MS, the collision-gas pressure is normally set at a level where the detection sensitivity to a number of target compounds will be high on average. This is not merely because the task of setting the collision-gas pressure at an optimum collision-gas pressure for each compound is troublesome when there are a large number of compounds to be analyzed. Another reason is that it is difficult to completely separate all compounds by the liquid chromatogram or gas chromatograph; in some cases, the elution times of two or more compounds overlap each other, making the determination of the optimum collision-gas pressure complicated and difficult.

For the previously described reasons, when a simultaneous multicomponent analysis is performed by an MRM measurement using a conventional LC/MS or GC/MS, the collision-gas pressure for each compound is not always set at an optimum level in terms of the detection sensitivity. This has been one factor that deteriorates the quantitative accuracy in the simultaneous multicomponent analysis.

Furthermore, to conduct an MRM measurement with the collision-gas pressure set at an optimum level for a target compound in the previously described manner, the analysis operator needs to previously investigate the optimum collision-gas pressure for that compound. For this purpose, the analysis operator must prepare a plurality of analysis condition files with the collision-gas pressure set at a plurality of different levels, perform the MRM measurement a plurality of times according to those analysis condition files, and compare the obtained results, or to perform the MRM measurement for the target compound while manually changing the collision-gas pressure so as to locate the optimum level of the collision-gas pressure. In any case, the task is significantly cumbersome. In particular, a considerable amount of time is needed to find the optimum collision-gas pressures for a large number of compounds.

CITATION LIST

Patent Literature

Patent Literature 1: JP 2012-104389 A

SUMMARY OF INVENTION

Technical Problem

The present invention has been developed to solve the previously described problems. Its primary objective is to provide a chromatograph mass spectrometer which can detect an ion originating from each compound with a high level of sensitivity even in a simultaneous multicomponent analysis by an MRM or similar measurement, and thereby achieve a high level of quantitative accuracy while avoiding an omission of the detection.

Another objective of the present invention is to provide a chromatograph mass spectrometer which can conveniently and efficiently perform the task of searching for an optimum or nearly optimum collision-gas pressure for detecting a compound with a high level of sensitivity.

Solution to Problem

The present invention developed for solving the previously described problems is a chromatograph mass spectrometer including a chromatograph for separating compounds in a sample and a mass analyzer for making an ion having a specific mass-to-charge ratio among the ions originating from a compound in a sample separated by the chromatograph undergo a dissociation by a collision with collision gas within a collision cell and for detecting a product ion produced by the dissociation, the chromatograph mass spectrometer including:

a) a gas supplier for supplying the collision gas to the collision cell;

b) a compound information storage section for storing retention time information and optimum collision-gas pressure information for each compound; and c) an analysis controller for retrieving the retention time information and the optimum collision-gas pressure information for a target compound designated as a measurement target from the compound information storage section, and for controlling the gas supplier based on the retrieved information so as to regulate the collision-gas pressure according to the timing at which the target compound is introduced from the chromatograph into the mass analyzer.

The analysis controller may perform the control so as to switch the collision-gas pressure based on the retention time information of the target compound during the execution of the measurement. Alternatively, it is also possible to prepare a sequence (program) for the control of the collision-gas pressure before the execution of the measurement, since the target compound is known beforehand, i.e. in advance of the execution of the measurement.

Accordingly, as one mode of the present invention, the analysis controller may include:

c1) an analysis condition determiner for retrieving, in advance of an execution of a measurement, the retention time information and the optimum collision-gas pressure information for a target compound designated as a measurement target from the compound information storage section, and for determining, based on the retrieved information, analysis condition information showing a change in the collision-gas pressure with respect to the lapse of time in the measurement; and c2) a control executer for controlling the gas supplier according to the analysis condition information when the measurement is executed.

In the chromatograph mass spectrometer according to the present invention, for example, the compound information storage section is created beforehand based on the result of a measurement performed by a user (analysis operator) for determining the relationship between the collision-gas pressure and the signal strength for each compound. The minimum requirement of the optimum collision-gas information is to include either a value of the collision-gas pressure which gives the highest detection sensitivity or a control value (e.g. the opening of a value in the gas supplier) for realizing such a collision-gas pressure. However, as will be described later, it is necessary in some cases to additionally include information showing the relationship between the collision-gas pressure and the signal strength in order to determine the optimum collision-gas pressure for a plurality of compounds whose elution times overlap each other.

For example, when a number of target compounds are designated as the target of a simultaneous multicomponent analysis by the analysis operator, the analysis condition determiner in the analysis controller retrieves, from the compound information storage section, the retention time information and the optimum collision-gas pressure information corresponding to each target compound. Subsequently, the analysis condition determiner prepares a control sequence (e.g. an analysis condition table which shows the change in the collision-gas pressure with respect to the lapse of time) so that, for each period of time where one target compound is introduced into the mass analyzer, the collision-gas pressure in the collision cell is set at the optimum collision-gas pressure for that target compound. After the measurement is initiated, the control executer in the analysis controller regulates the collision-gas pressure in the collision cell by controlling the gas supplier according to the prepared control sequence.

By this operation, the collision-gas pressure is set at an optimum or nearly optimum level for each of the target compounds sequentially introduced into the mass analyzer after being separated by the chromatograph. Consequently, ions originating from any target compound are dissociated with a high level of dissociation efficiency, so that the product ions can be detected with a high level of sensitivity.

If a plurality of compounds contained in the sample are temporally separated to a sufficient degree by the chromatograph, the elution times of the target compounds do not overlap each other and one optimum collision-gas pressure can be selected for each specific point in time. On the other hand, for example, if there are a plurality of target compounds whose retention times are extremely close to each other, the elution times of those target compounds overlap each other. In that case, if the optimum collision-gas pressure for one of the overlapping compounds is simply selected, the collision-gas pressure may be inappropriate for the other overlapping compounds, which means that the ion dissociation efficiency for these compounds may not be very high.

Accordingly, in the chromatograph mass spectrometer according to the present invention, if there are a plurality of target compounds whose elution times overlap each other, it is preferable to adopt one of the following modes.

As the first mode of the present invention, the analysis controller may be configured so that, when there are a plurality of target compounds whose elution times overlap each other, the analysis controller designates the arithmetic mean or geometric mean of the optimum collision-gas pressures respectively corresponding to the target compounds as the optimum collision-gas pressure for the elution time where the plurality of target compounds overlap each other.

According to this configuration, the optimum collision-gas pressure for the elution time can be easily computed, since it is merely necessary to calculate a mean value of the respective optimum collision-gas pressures of the plurality of target compounds. It is unnecessary to prepare the information showing the relationship between the collision-gas pressure and the signal strength, since the computation can be performed as long as the value of the optimum collision-gas pressure for each compound is known.

As the second mode of the present invention, the compound information storage section may include information showing the relationship between the collision-gas pressure and the signal strength for each compound, and the analysis controller may be configured so that, when there are a plurality of target compounds whose elution times overlap each other, the analysis controller designates, as the optimum collision-gas pressure for the elution time where the plurality of target compounds overlap each other, a gas pressure corresponding to an intersection of the curves which respectively show the relationship between the collision-gas pressure and the signal strength for the plurality of target compounds.

As the third mode of the present invention, the compound information storage section may include information showing the relationship between the collision-gas pressure and the signal strength for each compound, and the analysis controller may be configured so that, when there are three or more target compounds whose elution times overlap each other, the analysis controller determines the optimum collision-gas pressure for the elution time where the three or more target compounds overlap each other using the curves which respectively show the relationship between the collision-gas pressure and the signal strength for two target compounds having the largest difference in the optimum collision-gas pressure among the three or more target compounds.

As the fourth mode of the present invention, the compound information storage section may include information showing the relationship between the collision-gas pressure and the signal strength for each compound, and the analysis controller may be configured so that, when there are a plurality of target compounds whose elution times overlap each other, the analysis controller calculates both the arithmetic mean of the optimum collision-gas pressures respectively corresponding to the plurality of target compounds and the geometric mean of the optimum collision-gas pressures respectively corresponding to the plurality of target compounds as candidates of the optimum collision-gas pressure for the elution time where the plurality of target compounds overlap each other, determines another candidate of the optimum collision-gas pressure for the elution time where the plurality of target compounds overlap each other using the curves which respectively show the relationship between the collision-gas pressure and the signal strength for the plurality of target compounds, and selects, as the optimum collision-gas pressure for the elution time where the plurality of target compounds overlap each other, the candidate of the optimum collision-gas pressure which causes the smallest amount of decrease in the signal strength for the plurality of target compounds among the candidates of the optimum collision-gas pressure.

According to the fourth mode, as compared to the first through third modes, although a longer period of time is needed to determine the optimum collision-gas pressure for the elution time where a plurality of target compounds overlap each other, those target compounds can be detected with the highest level of sensitivity on the general basis.

Any of the first through fourth modes has the advantage that the optimum collision-gas pressure for the elution time where a plurality of target compounds overlap each other can be automatically determined without inconveniencing the analysis operator. However, since the optimum collision-gas pressure is determined so as to generally enhance the sensitivity to the plurality of target compounds whose elution times overlap each other, it is usually impossible to meet the demand of an analysis operator who desires to perform the measurement with a particularly high level of sensitivity for one specific compound in the plurality of target compounds.

Accordingly, in the chromatograph mass spectrometer according to the present invention, it is more preferable to additionally provide a selection instructor for allowing an analysis operator to select which of the collision-gas pressure automatically determined according to one of the first through fourth modes and a collision-gas pressure entered by the analysis operator should be designated as the optimum collision-gas pressure for the elution time where the plurality of target compounds overlap each other when there are a plurality of target compounds whose elution times overlap each other.

The selection instructor may preferably be configured so that, only when the signal strength of at least one of the plurality of target compounds whose elution times overlap each other falls outside a predetermined range from the highest signal strength of that compound under the collision-gas pressure automatically determined according to one of the first through fourth modes, the selection instructor allows the analysis operator to select which of the automatically determined collision-gas pressure and the collision-gas pressure entered by the analysis operator should be designated as the optimum collision-gas pressure for the elution time where the plurality of target compounds overlap each other.

According to this configuration, if the automatically determined optimum collision-gas pressure is not suited for the measurement intended by the analysis operator, the analysis operator can arbitrarily set the collision-gas pressure according to the intention. Therefore, for example, it is possible to set the collision-gas pressure so that the sensitivity will be particularly high for one of the plurality of target compounds whose elution times overlap each other.

In the case where the chromatograph mass spectrometer according to the present invention is provided with the selection instructor through which the gas pressure entered by the analysis operator can be selected in the previously described manner, it is preferable to additionally provide a display processor for displaying, on the screen of a display unit, a graph showing the relationship between the collision-gas pressure and the signal strength for a plurality of target compounds whose elution times overlap each other. The graph displayed on the screen of the display unit allows the analysis operator to grasp the relationship between the collision-gas pressure and the signal strength for each target compound and set an appropriate collision-gas pressure based on this relationship.

In order to make the system easier to operate for analysis operators in setting the appropriate collision-gas pressure, the following configuration may preferably be adopted:

a gas pressure indicator is additionally provided for allowing the analysis operator to specify a collision-gas pressure on the graph displayed on the screen of the display unit; and the display processor displays the signal strengths of the plurality of target compounds whose elution times overlap each other under the collision-gas pressure specified by the gas pressure indicator.

Preferably, the chromatograph mass spectrometer according to the present invention may further include:

a preliminary measurement executer for changing the collision-gas pressure by the gas supplier in a continuous or stepwise manner, with a sample containing the same compound introduced in the mass analyzer, and for acquiring the signal strength of a product ion originating from the compound for every change in the collision-gas pressure; and an optimum gas pressure extracter for determining the collision-gas pressure at which the peak value of the signal strength is maximized, based on a change in the signal strength corresponding to the change in the collision-gas pressure obtained by the preliminary measurement executer, and the collision-gas pressure determined by the optimum gas pressure extractor is used as the optimum collision-gas pressure information to be stored in the compound information storage section.

In this system, when the preliminary measurement for a compound is performed by the preliminary measurement executer, a sample containing the target compound can be introduced into the mass analyzer by either a flow injection method or infusion method in place of the sample which has passed through the column of the chromatograph.

In the case of the flow injection method, the concentration of the compound in the sample introduced into the mass analyzer changes with time. Therefore, it is preferable to repeat the sample injection a plurality of times while changing the collision-gas pressure in a stepwise manner at the timing of the sample injection. In the case of the infusion method, the concentration of the compound in the sample introduced into the mass analyzer is at a constant level. Therefore, it is preferable to change the collision-gas pressure in a stepwise or continuous manner while the compound is being introduced.

By this configuration, the optimum collision-gas pressure for each individual compound is conveniently determined in an automatic manner, i.e. without requiring the analysis operator to manually regulate the collision-gas pressure or prepare a plurality of analysis condition files with different collision-gas pressures. Consequently, the burden on the analysis operator will be reduced, and the process of determining the optimum collision-gas pressures for a number of compounds will be performed in a shorter period of time, so that the analysis can be performed efficiently.

Naturally, the previously described technique of extracting the optimum collision-gas pressure by the preliminary measurement executer and the optimum gas pressure extractor may also be used in the case of determining the optimum collision-gas pressure which is not intended to be stored in the compound information storage section.

Accordingly, the second chromatograph mass spectrometer according to the present invention developed for solving the previously described problems is a chromatograph mass spectrometer including a chromatograph for separating compounds in a sample and a mass analyzer for making an ion having a specific mass-to-charge ratio among the ions originating from a compound in a sample separated by the chromatograph undergo a dissociation by a collision with collision gas within a collision cell and for detecting a product ion produced by the dissociation, the chromatograph mass spectrometer including:

a) a gas supplier for supplying the collision gas to the collision cell;

b) a preliminary measurement executer for changing the collision-gas pressure by the gas supplier in a continuous or stepwise manner, with a sample containing the same compound introduced in the mass analyzer, and for acquiring the signal strength of a product ion originating from the compound for every change in the collision-gas pressure;

c) an optimum gas pressure extractor for determining the collision-gas pressure at which the peak value of the signal strength is maximized, based on a change in the signal strength corresponding to the change in the collision-gas pressure obtained by the preliminary measurement executer; and d) an analysis controller for controlling the gas supplier, using the optimum collision-gas pressure obtained by the optimum gas pressure extractor, so as to regulate the collision-gas pressure in a measurement in which a sample containing the compound is introduced into the chromatograph, at least when the compound is introduced from the chromatograph into the mass analyzer.

By the second chromatograph mass spectrometer according to the present invention, as already described, the optimum collision-gas pressure for each individual compound is conveniently determined in an automatic manner, i.e. without requiring the analysis operator to manually regulate the collision-gas pressure or prepare a plurality of analysis condition files with different collision-gas pressures. Consequently, the burden on the analysis operator will be reduced, and the process of determining the optimum collision-gas pressures for a number of compounds will be performed in a shorter period of time, so that the analysis can be performed efficiently.

Similarly to the first one, in the second chromatograph mass spectrometer according to the present invention, when the preliminary measurement for a compound is performed by the preliminary measurement executer, a sample containing the target compound can be introduced into the mass analyzer by either a flow injection method or infusion method, in place of the sample which has passed through the column of the chromatograph.

Advantageous Effects of the Invention

In the chromatograph mass spectrometer according to the present invention, while a plurality of compounds contained in the sample are individually introduced into the mass spectrometer, the collision-gas pressure is regulated according to the timing of the introduction of each compound so that the ion dissociation efficiency within the collision cell will be at the highest or nearly highest level. Consequently, any one of the compounds can be detected with a sufficiently high level of sensitivity, so that a high level of quantitative accuracy is achieved and even such compounds that are contained in extremely small quantities will be completely detected.

With the second chromatograph mass spectrometer according to the present invention, the optimum collision-gas pressure for individually analyzing various compounds with a high level of sensitivity can be efficiently investigated without inconveniencing the analysis operator.

DESCRIPTION OF EMBODIMENTS

A liquid chromatograph triple quadrupole mass spectrometer as one embodiment of the present invention (which is hereinafter called the "LC/MS/MS" according to common practice) is hereinafter described with reference to the attached drawings.

Figure 1:
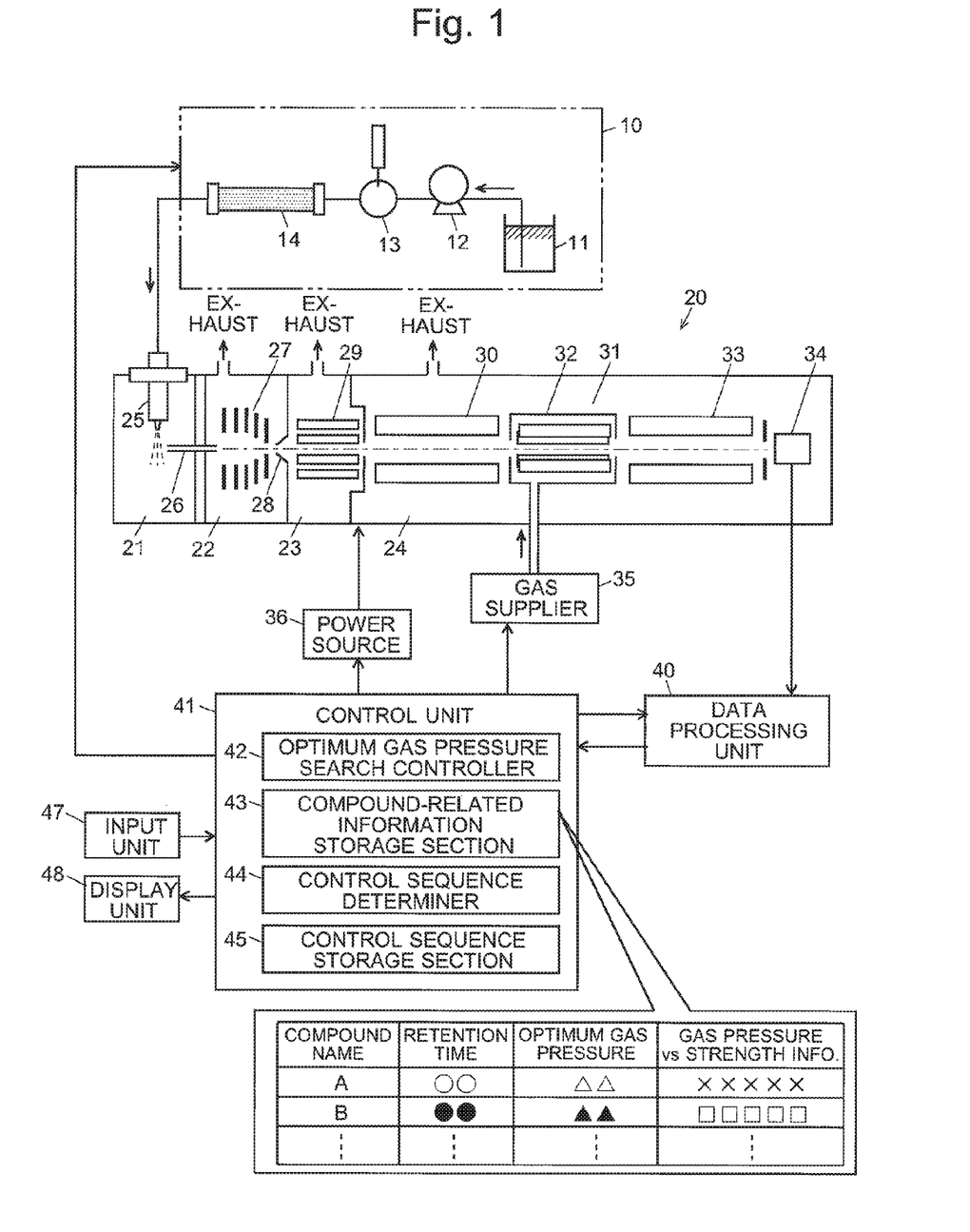
FIG. 1 is a schematic configuration diagram of the main components of a liquid chromatograph triple quadrupole mass spectrometer according to one embodiment of the present invention.

FIG. 1 is a schematic configuration diagram of the main components of the LC/MS/MS of the present embodiment.

In the LC/MS/MS of the present embodiment, the liquid chromatograph unit 10 includes a mobile-phase container 11 holding a mobile phase, a liquid-sending pump 12 for drawing and supplying the mobile phase at a fixed flow rate, an injector 13 for injecting a predetermined amount of prepared sample into the mobile phase, and a column 14 for temporally separating various compounds contained in the sample. The liquid-sending pump 12 draws the mobile phase from the mobile-phase container 11 and supplies it to the column 14 at a fixed flow rate. When a certain amount of sample liquid is introduced from the injector 13 into the mobile phase, the sample is carried by the mobile phase into the column 14. While passing through this column 14, various compounds in the sample are temporally separated and eluted from the exit port of the column 14, to be introduced into the mass spectrometer 20.

The mass spectrometer 20 has the configuration of a multistage differential pumping system having an ionization chamber 21 maintained at substantially atmospheric pressure and an analysis chamber 24 evacuated to a high degree of vacuum by a high-performance vacuum pump (not shown), between which first and second intermediate chambers 22 and 23 are provided having their degrees of vacuum increased in a stepwise manner. The ionization chamber 21 is provided with an electrospray ionization (ESI) probe 25 for spraying a sample solution while giving electric charges to this solution. The ionization chamber 21 communicates with the first intermediate vacuum chamber 22 in the next stage through a thin heated capillary 26. The first and second intermediate chambers 22 and 23 are separated from each other by a skimmer 28 having a small hole at its apex. Ion guides 27 and 29 for transporting ions to the subsequent section while converging them are provided in the first and second intermediate vacuum chambers 22 and 23, respectively.

Within the analysis chamber 24, a collision cell 31 containing a multipole ion guide 32 is provided between front and rear quadrupole mass filters 30 and 33 which separate ions according to their mass-to-charge ratios. Additionally, an ion detector 34 is placed behind the rear quadrupole mass filter 33. A gas supplier 35 supplies collision gas (e.g. argon or nitrogen) to the inside of the collision cell 31. A power source 36 applies predetermined forms of voltage to the ESI probe 25, ion guides 27, 29 and 32, quadruple mass filters 30 and 33, as well as other components, respectively.

In this mass spectrometer 20, when the eluate from the exit port of the column 14 reaches the tip portion of the ESI probe 25, the eluate is sprayed into the ionization chamber 21 while receiving electric charges. The electrically charged droplets produced by the spraying process are divided into smaller sizes by colliding with the ambient air as well as by the Coulomb repulsive force. During this process, the solvent in the droplets vaporizes, and ions derived from the compounds in the droplets are ejected. The thereby produced ions are sent through the heated capillary 26 into the first intermediate vacuum chamber 22, where the ions are converged by the ion guide 27 and sent through the small hole at the apex of the skimmer 28 into the second intermediate vacuum chamber 23. Then, the compound-derived ions are converged by the ion guide 29 and sent into the analysis chamber 24, where they are introduced into the space extending along the longitudinal axis of the front quadrupole mass filter 30. Naturally, the ionization method is not limited to the ESI; other atmospheric pressure ionization methods may also be used, such as atmospheric pressure chemical ionization (APCI) or atmospheric pressure photoionization (APPI).

In the mass spectrometer 20, when an MS/MS analysis is performed, a predetermined form of voltage (produced by superposing a radio-frequency voltage on a direct-current voltage) is applied from the power source 36 to each of the rod electrodes of the front and rear quadrupole mass filters 30 and 33. Meanwhile the collision gas is continuously or intermittently supplied from the gas supplier 35 to the inside of the collision cell 31. Among the various ions sent into the front quadrupole mass filter 30, only an ion having a specific mass-to-charge ratio m/z corresponding to the voltage applied to the rod electrodes of the front quadrupole mass filter 30 is allowed to pass through this filter 30 and be introduced into the collision cell 31 as the precursor ion.

Within the collision cell 31, the precursor ion collides with the collision gas and becomes dissociated, whereby various product ions are produced. The various product ions produced in this manner are introduced into the rear quadrupole mass filter 33, where only a product ion having a specific mass-to-charge ratio corresponding to the voltage applied to the rod electrodes of the rear quadrupole mass filter 33 is allowed to pass through this filter 33, to eventually arrive at and be detected by the ion detector 34. The ion detector 34 produces a detection signal corresponding to the number of incident ions and sends this signal to a data processing unit 40.

Based on the detection signals which are sequentially fed with the passage of time, the data processing unit 40 performs various processes; e.g. it creates a mass spectrum and chromatogram (e.g. total in chromatogram or mass chromatogram) and performs a quantitative analysis based on the chromatogram. The control unit 41, which is equipped with an input unit 47 and display unit 48, has the function of controlling the operations of various components in the system, such as the liquid-sending pump 20 and the injector 13 in the liquid chromatograph unit 10 as well as the power source 36 and the gas supplier 35 in the mass spectrometer 20. The control unit 41 includes, as its characteristic functional blocks, an optimum gas pressure search controller 42, compound-related information storage section 43, control sequence determiner 44, control sequence storage section 45, and other elements.

At least some of the functions of the control unit 41 and the data processing unit 40 can be realized using a personal computer as a hardware resource by running, on this personal computer, a dedicated controlling and processing software program previously installed on the computer.

The LCMS/MS of the present embodiment has the function of automatically searching for the collision-gas pressure at which the detection sensitivity to the product ion is maximized, i.e. the optimum collision-gas pressure, based on the result of an actual measurement of a sample containing the target compound. Hereinafter, one example of the operation of automatically searching for the optimum collision-gas pressure using this function is initially described.

In the process of searching for the optimum collision-gas pressure, the introduction of the liquid sample into the mass spectrometer 20 is performed by either a flow injection method or infusion method without passing the sample through the column 14 of the liquid chromatograph unit 10.

Figure 2A:
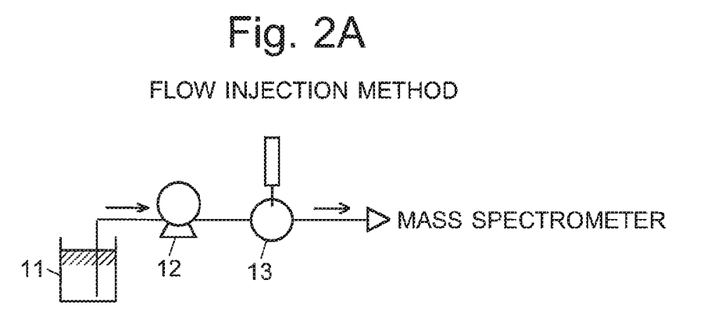
FIGS. 2A and 2B illustrate a process of searching for the optimum collision-gas pressure using a flow injection method in the liquid chromatograph triple quadrupole mass spectrometer of the present embodiment.
Figure 2B:
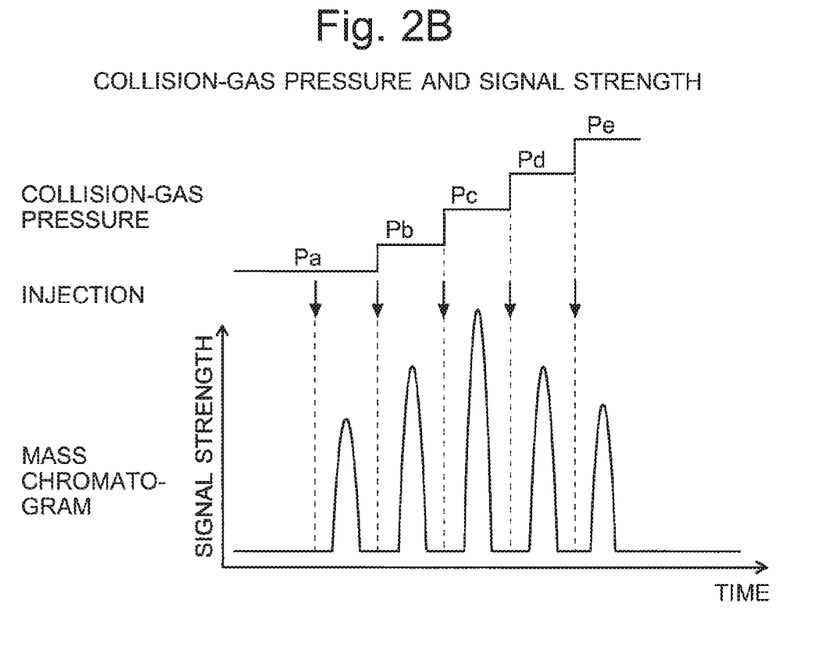

FIG. 2A illustrates the configuration of a sample introduction system employing the flow injection method, and FIG. 2B illustrates the process of automatically searching for the optimum collision-gas pressure in the present example.

As shown in FIG. 2B, the sample introduction system employing the flow injection method is equivalent to the liquid chromatograph section 10 from which the column 14 is removed. A predetermined amount of sample solution is injected from the injector 13 into the mobile phase (solvent) supplied by the liquid-sending pump 12 at a fixed flow rate. The sample solution contains a known compound (normally, only a single kind of compound). While being carried forward by the mobile phase, this compound in the sample solution is slightly diffused along the flowing direction and introduced into the mass spectrometer 20 with a certain extent of temporal width.

As shown in FIG. 2B, the optimum gas pressure search controller 42 operates the gas supplier 35 at the timing of the injection of the sample from the injector 13 (at the points in time indicated by the downward arrows in FIG. 2B) so as to sequentially increase the collision-gas pressure among five levels from Pa to Pe. The optimum gas pressure search controller 42 also controls the power source 36 so as to perform the MRM measurement in which the mass-to-charge ratio of the precursor ion and that of the product ion corresponding to the compound contained in the sample are monitored as the targets. Every time the sample is injected from the injector 13, an ion having a specific mass-to-charge ratio originating from the compound contained in the sample is selected by the front quadrupole mass filter 30. This ion is subsequently dissociated in the collision cell 31 under the predetermined collision-gas pressure. Among the various product ions produced by the dissociation process, an ion having a specific mass-to-charge ratio is selected by the rear quadrupole mass filter 33. This ion eventually arrives at the ion detector 34 and is thereby detected. Based on the thereby produced detection signal, the data processing unit 40 creates a mass chromatogram at the mass-to-charge ratio of the specified product ion.

As the collision-gas pressure is changed, the ion dissociation efficiency changes, and consequently, the signal strength of the peak originating from the same ion on the mass chromatogram changes, as shown in FIG. 2B. The optimum gas pressure search controller 42 compares the peak-top signal intensities of the peaks (or the areas of the peaks) on the mass chromatogram, and extracts the collision-gas pressure which gives the highest signal intensity as the optimum collision-gas pressure for that compound. In the example of FIG. 2B, the peak-top signal intensity reaches the highest level when the collision-gas pressure is Pc. Accordingly, it is determined that Pc is the optimum collision-gas pressure.

In FIG. 2B, the collision-gas pressure is changed among the five levels. It is also possible to search for the collision-gas pressure which gives the highest signal strength while changing the collision-gas pressure in smaller steps. Alternatively, it is preferable to determine a more appropriate gas-pressure value by performing the search in two stages with different steps, i.e. a rough search in which the collision-gas pressure is changed in larger steps to roughly locate the collision-gas pressure at which the highest signal strength is obtained among the set pressure values, and a fine search in which the collision-gas pressure is changed in smaller steps within the vicinity of the roughly located gas pressure to more accurately search for the collision-gas pressure which gives the highest signal strength.

Figure 3A:
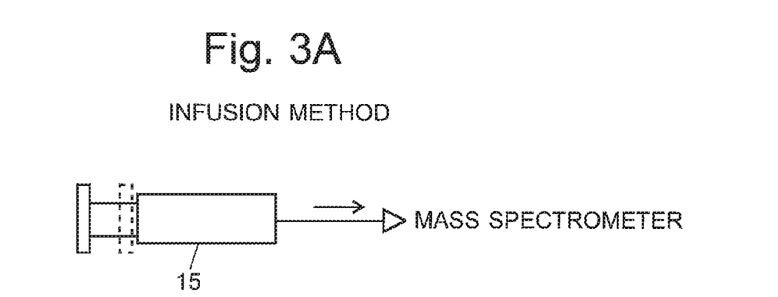
FIGS. 3A and 3B illustrate a process of searching for the optimum collision-gas pressure using an infusion method in the liquid chromatograph triple quadrupole mass spectrometer of the present embodiment.
Figure 3B:
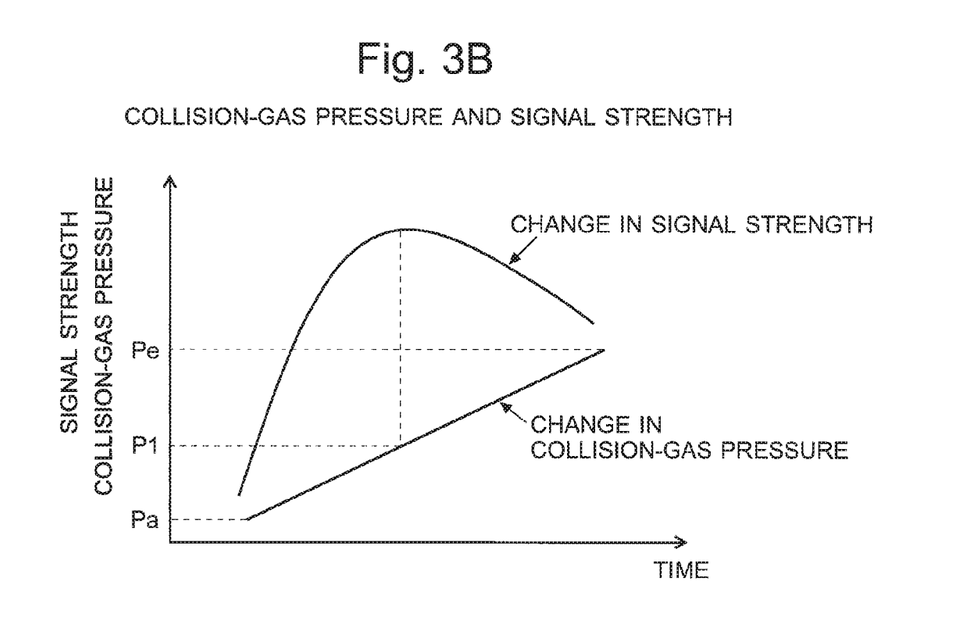

FIG. 3A illustrates the configuration of a sample introduction system employing the infusion method, and FIG. 3B illustrates the process of automatically searching for the optimum collision-gas pressure in the present example.

As shown in FIG. 3A, the sample introduction system employing the infusion method includes a syringe pump 15. By this syringe pump 15, a liquid sample containing a compound is introduced into the mass spectrometer 20 at a fixed flow rate. As shown in FIG. 3B, while the liquid sample is being introduced into the mass spectrometer 20, the optimum gas pressure search controller 42 operates the gas supplier 35 so as to continuously increase the collision-gas pressure from Pa to Pe. The rate of change in the collision-gas pressure should be set taking into account the fact that, in normal situations, the collision-gas pressure in the collision cell 31 does not suddenly change.

In this case, a substantially fixed amount of precursor ion originating from the target compound is continuously introduced into the collision cell 31 and undergoes dissociation with the ion dissociation efficiency which depends on the collision-gas pressure. The thereby generated product ion reaches the ion detector 34. An observation of the temporal change in the signal strength of the product ion originating from the target compound will result in a waveform having a large peak in which the signal strength reaches the highest level at a certain point in time, as shown in FIG. 3B. The optimum gas pressure search controller 42 locates the collision-gas pressure which gives the highest signal strength in this peak waveform, and designates this collision-gas pressure as the optimum collision-gas pressure for the compound concerned. In the example of FIG. 3B, it is determined that P1 is the optimum collision-gas pressure.

The process of automatically searching for the optimum collision-gas pressure based on a previous measurement described thus far is performed for all of the target compounds to determine the optimum collision-gas pressure for each compound. The relationship between the collision-gas pressure and the signal strength value over a predetermine range of collision-gas pressure is also previously determined in an appropriate form, such as a table format or approximate formula. The optimum collision-gas pressure, the information showing the relationship between the collision-gas pressure and the signal strength value (e.g. a table or approximate formula), as well as the retention time are related to each compound and stored in the compound-related information storage section 43. In FIG. 1, one example of the information stored in the compound-related information storage section 43 is shown. The retention time of each compound may be an actually measured result or a value based on some information obtained from a commonly available compound information database or other sources.

Instead of the retention time, the retention index, relative retention ratio or similar value may also be used. Additionally, the value of the collision gas may be replaced with a value for controlling the collision-gas pressure in the collision cell 31, such as the opening of a valve in the gas supplier 35. The information showing the relationship between the gas pressure and the signal strength value is dispensable; this information is required when a specific process is performed (which will be described later).

With the retention time, optimum collision-gas pressure, and information showing the relationship between the gas pressure and the signal strength value for various compounds stored in the previously described manner, a simultaneous multicomponent analysis by an MRM measurement is performed. One example of the measurement operation is hereinafter described.

To perform a simultaneous multicomponent analysis using an MRM measurement, an analysis operator specifies the kinds of compounds to be analyzed, the mass-to-charge ratio of the precursor ion and that of the product ion for each compound, as well as other measurement conditions from the input unit 47. The control sequence determiner 44 retrieves the retention time, optimum collision-gas pressure, and information showing the relationship between the gas pressure and the signal strength for all specified compounds from the compound-related information storage section 43. In ideal situations, each compound which elutes from the column 14 and is introduced into the mass spectrometer 20 has the highest concentration at its retention time. However, in practice, the timing of the elution of the compound becomes earlier or later than the retention time due to various factors. Accordingly, the control sequence determiner 44 computes the elution time for each compound allowing for a predetermined width of time as the margin around its retention time.

In an MRM measurement, the analysis operator sets the starting time and ending time of the measurement for each compound as one of the measurement conditions taking into account the retention time of the compound. Accordingly, the period of time from the starting time to the ending time measurement set in the measurement conditions may be used as the elution time. In any case, the elution time specified for one compound includes the retention time corresponding to that compound.

Figure 4A:
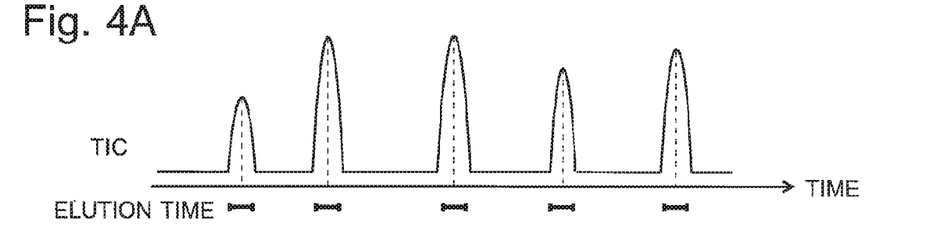
FIGS. 4A and 4B show examples of the relationship among the retention times of a plurality of compounds in a simultaneous multicomponent analysis.
Figure 4B:
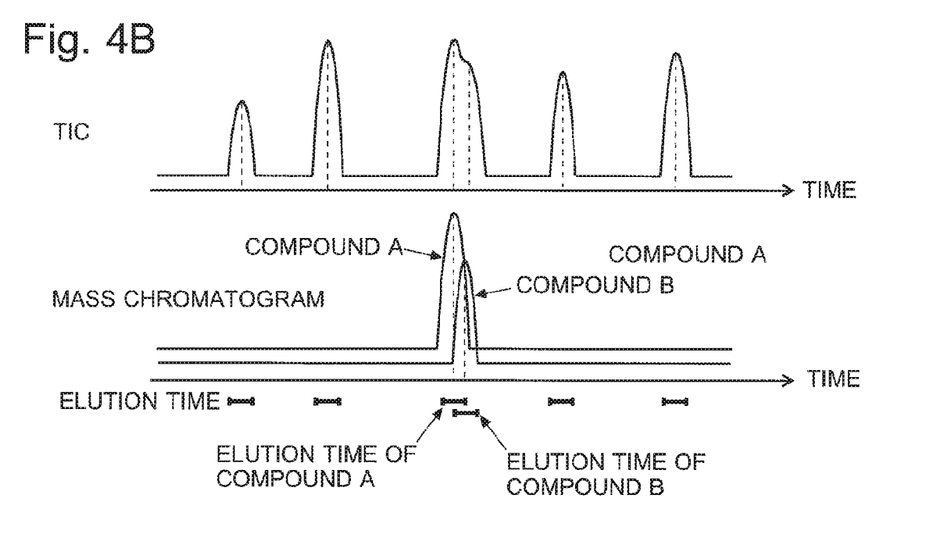

FIGS. 4A and 4B are chromatograms showing examples of the relationship between the retention times of a plurality of compounds in a simultaneous multicomponent analysis. FIG. 4A is the case where the retention times of the compounds are sufficiently separated, while FIG. 4B is the case where there are compounds whose retention times are close to each other.

As shown in FIG. 4A, when the retention times of the compounds are sufficiently separated, the elution times corresponding to those compounds do not temporally overlap each other. Therefore, it is unnecessary to simultaneously detect ions originating from a plurality of compounds, so it is easy to determine the optimum collision-gas pressure for each elution time. Accordingly, in this case, for an elution time in which only one kind of compound appears, the control sequence determiner 44 simply adopts the optimum collision-gas pressure related to that compound as the optimum collision-gas pressure.

On the other hand, as shown in FIG. 4B, when there are a plurality of compounds whose retention times are so close to each other that their elution times overlap each other, i.e. when it is necessary to simultaneously detect a plurality of compounds (to be exact, by a time-division process at short intervals of time, and not simultaneously), simply selecting the optimum collision-gas pressure for one compound may cause a significant decrease in the detection sensitivity to the other compounds. Therefore, the control sequence determiner 44 uses one of the following methods to determine the optimum collision-gas pressure for the entire elution time corresponding to the compounds whose retention times overlap each other.

[First Method]

As one example, suppose that there are two compounds A and B whose elution times overlap each other. In this case, the control sequence determiner 44 reads the optimum collision-gas pressure information for each of the compounds A and B from the compound-related information storage section 43. Subsequently, it calculates the arithmetic mean or geometric mean of the optimum collision-gas pressures of the two compounds, and designates the calculated result as the optimum collision-gas pressure for the elution time concerned. Even when there are three or more compounds whose elution times overlap each other, the arithmetic mean or geometric mean of the optimum collision-gas pressures of those compounds can be similarly used. The present method does not use the information showing the relationship between the gas pressure and the signal strength. Therefore, this information does not need to be stored in the compound-related information storage section 43.

[Second Method]

Figure 5:
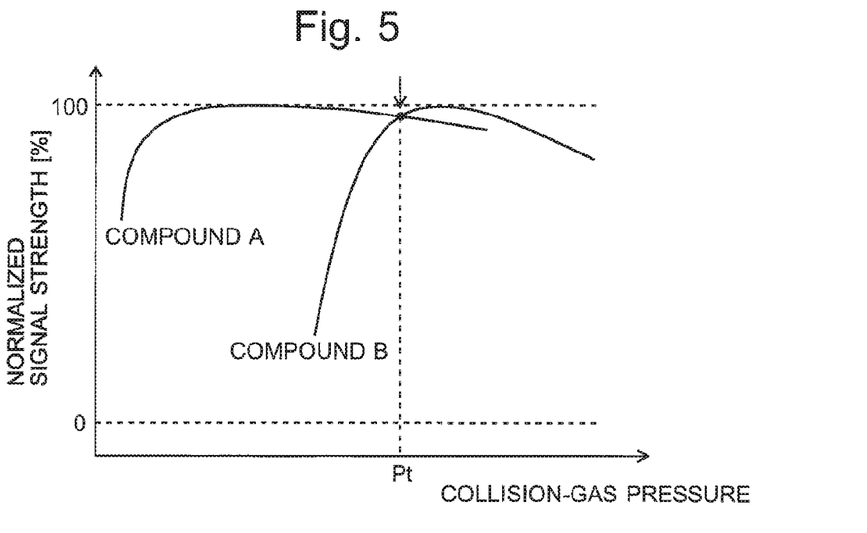
FIG. 5 illustrates one example of the method for calculating the optimum collision-gas pressure in the case where the elution times of two compounds overlap each other.

As one example, suppose that there are two compounds A and B whose elution times overlap each other. In this case, the control sequence determiner 44 reads the information showing the relationship between the gas pressure and the signal strength for each of the compounds A and B from the compound-related information storage section 43. Subsequently, as shown in FIG. 5, it determines the intersection of the curve showing the relationship between the gas pressure and the signal strength for compound A and the curve showing the relationship between the gas pressure and the signal strength for compound B, and calculates the collision-gas pressure Pt corresponding to that intersection. This pressure Pt is eventually adopted as the optimum collision-gas pressure for the elution time where both compounds A and B are eluted.

As shown in FIG. 5, in the case of using the curves showing the relationship between the gas pressure and the signal strength for a plurality of compounds, the signal strength should be normalized so that the highest signal strength will be equal to 100%, in order to cancel out the effect of the difference in the absolute values of the signal strength.

Although the optimum collision-gas pressure derived from the intersection of the two curves is not perfectly optimum for any of the compounds, the selected collision-gas pressure is close to the optimum level and well balanced.

Next, consider the case where there are not two but three or more compounds whose elution times overlap with each other. Suppose that there are the three compounds X, Y and Z whose elution times overlap with each other. In this case, the control sequence determiner 44 reads the optimum collision-gas pressure information for each of the compounds X, Y and Z from the compound-related information storage section 43. Subsequently, it selects two compounds having the largest difference in the optimum collision-gas pressure, and reads the information showing the relationship between the gas pressure and the signal strength for each of the two compounds from the compound-related information storage section 43. In the example shown in FIG. 6, compounds X and Y are the two selected compounds.

Figure 6:
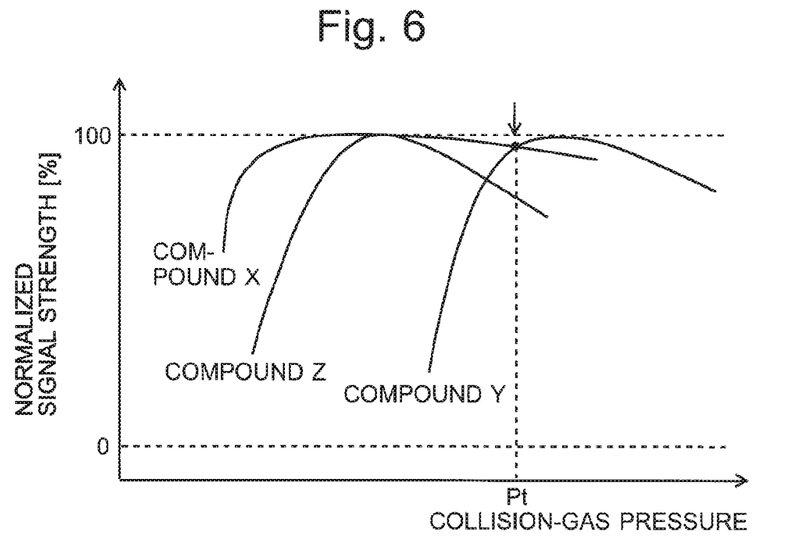
FIG. 6 illustrates one example of the method for calculating the optimum collision-gas pressure in the case where the elution times of three or more compounds overlap each other.

Subsequently, as shown in FIG. 6, the control sequence determiner 44 determines the intersection of the two curves showing the relationship between the gas pressure and the signal strength for the two compounds, calculates the collision-gas pressure Pt corresponding to that intersection, and adopts this pressure as the optimum collision-gas pressure for the entire elution time including the elution time where the compounds X, Y and Z are simultaneously eluted.

[Third Method]

If the second method is applied in the case where there are three or more compounds whose elution times overlap each other, the sensitivity to a compound which has not been used in the calculation of the intersection may be considerably decreased. To address this situation, it is possible to calculate the optimum collision-gas pressure by each of the first and second methods, designate the calculated values as the candidates, and select one candidate which causes the smallest decrease in the sensitivity to the compound which has not been used in the calculation of the intersection, i.e. one candidate which gives the highest level of sensitivity among those candidates.

Figure 7:
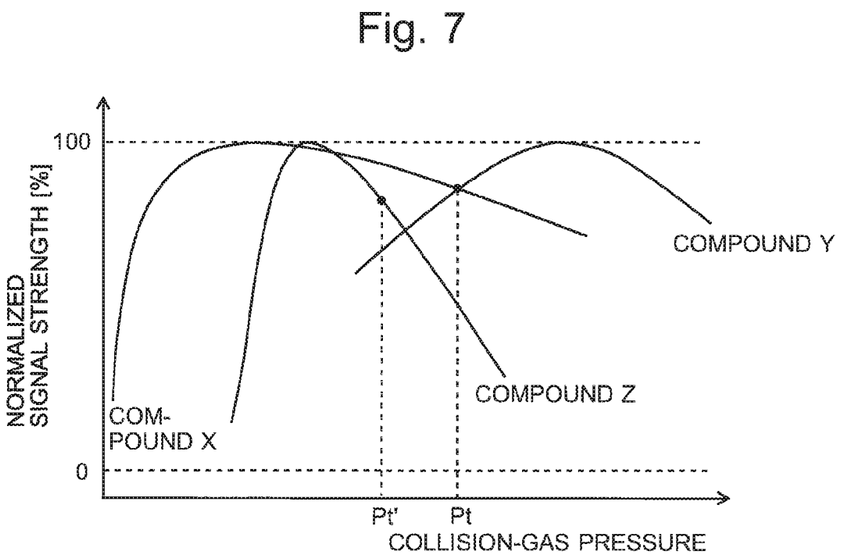
FIG. 7 illustrates one example of the method for calculating the optimum collision-gas pressure in the case where the elution times of three or more compounds overlap each other.

As one example, suppose that the three compounds X, Y and Z whose elution times overlap each other have the relationship between the collision-gas pressure and the signal strength as shown in FIG. 7. The collision-gas pressure determined by the second method is Pt, while the collision-gas pressure determined by the first method is Pt'. A comparison of the signal strengths which correspond to the collision-gas pressures Pt and Pt' on the curve showing the relationship between the collision-gas pressure and the signal strength for compound Z demonstrates that the signal strength at the collision-gas pressure Pt' is higher. Accordingly, this pressure can be adopted as the optimum collision-gas pressure for the entire elution time including the elution time where the compounds X. Y and Z are simultaneously eluted.

[Fourth Method]

Any of the first through third methods described thus far can be categorized as a technique aimed at achieving a high level of normalized signal strength on average for all of the plurality of compounds whose elution times overlap each other. However, there may be the case where the sensitivity to a compound which is actually detected at a low level of sensitivity should be given priority in determining the collision-gas pressure, or the case where the sensitivity to a specific compound should be given priority in determining the collision-gas pressure. Furthermore, the techniques of automatically determining the optimum-collision gas pressure in the previously described manner cannot completely eliminate the possibility of selecting a collision-gas pressure which causes the sensitivity to a specific compound to be extremely low. Considering these factors, it is preferable to leave room for a selection and/or instruction by an analysis operator instead of allowing the control sequence determiner 44 to completely and automatically determine the optimum collision-gas pressure.

Specifically, after the optimum collision-gas pressure for an elution time in which a plurality of compounds overlap each other has been calculated by one of the first through third methods, the control sequence determiner 44 displays the result on the screen of the display unit 48 along with a message requesting the analysis operator to determine whether or not the gas-pressure value needs any change. Checking the displayed result, the analysis operator either accepts the gas-pressure value (if the value is acceptable) or enters from the input unit 47 a different gas-pressure value (if the value needs to be changed). Upon receiving this entry, the control sequence determiner 44 adopts the value which has been manually changed by the analysis operator as the optimum collision-gas pressure for the elution time concerned.

Figure 8:
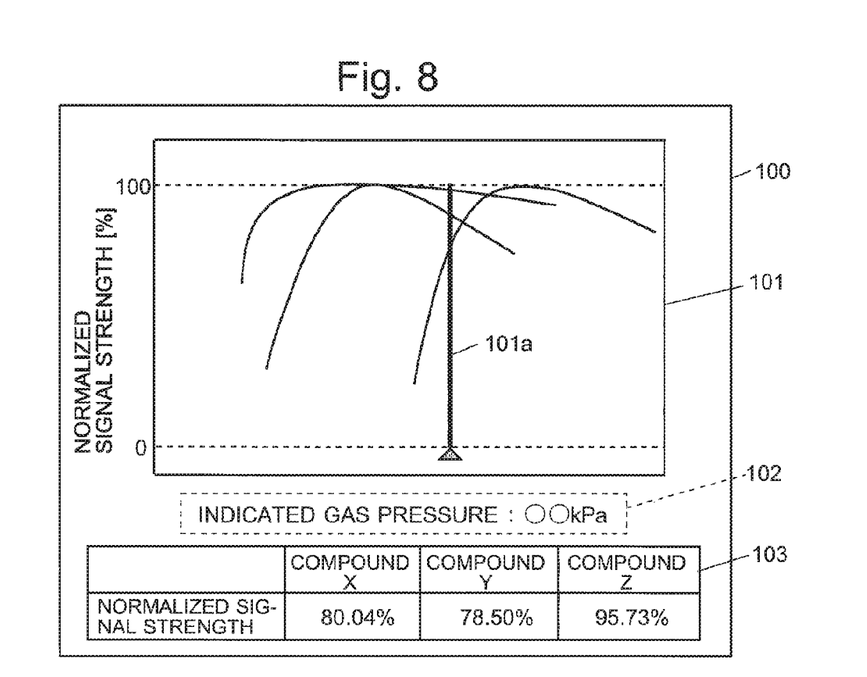
FIG. 8 shows one display example of the graph showing the relationship between the normalized signal strength and the collision-gas pressure in the liquid chromatograph triple quadrupole mass spectrometer of the present embodiment.

In order to allow the analysis operator to determine the appropriateness of the collision-gas pressure in the previously described manner, the relationship between the collision-gas pressure and the signal strength should be displayed in an easy-to-understand manner. Accordingly, in the case of requesting the confirmation or modification of the gas-pressure value by the analysis operator, it is preferable to display a collision-gas pressure check window 100 as shown in FIG. 8 on the display unit 48. The collision-gas pressure check window 100 includes a graph 101 showing the relationship between the collision-gas pressure and the signal strength for the mutually overlapping compounds, a gas-pressure indication field 102 showing the gas pressure indicated by the rod-shaped vertical marker 101a displayed on the graph 101, and a table 103 showing the normalized signal strength of each compound at the gas pressure indicated by the marker 101a. The marker 101a can be horizontally moved by an operation using the input unit 47 (e.g. a mouse or similar pointing device) and thereby enables the checking of the normalized signal strength of each compound at an arbitrary collision-gas pressure. With the help of such a display and operation, the analysis operator can locate an appropriate collision-gas pressure according to the purpose of the analysis or other factors and set that pressure as the optimum collision-gas pressure.

Constantly requesting the analysis operator to perform such a manual task of checking and changing the collision-gas pressure value may possibly deteriorate the operability of the system. Accordingly, for example, the system may be configured to automatically calculate the optimum collision-gas pressure by one of the first through third methods and subsequently request the analysis operator to perform the previously described task only when the calculated gas pressure causes the signal strength of at least one compound to decrease by an amount equal to or greater than a predetermined permissible value.

In the previously described manner, before the measurement of the sample is actually performed, the control sequence determiner 44 determines the optimum collision-gas pressure for the elution time of each compound to be analyzed, and prepares a gas-pressure control sequence so that the collision-gas pressure in the collision cell 31 will be set at the determined optimum collision-gas pressure at least within the elution time of that compound. The gas-pressure control sequence in the present context is a program which changes the collision-gas pressure with the passage of time. The prepared control sequence is stored in the control sequence storage section 45.

Figure 9A:
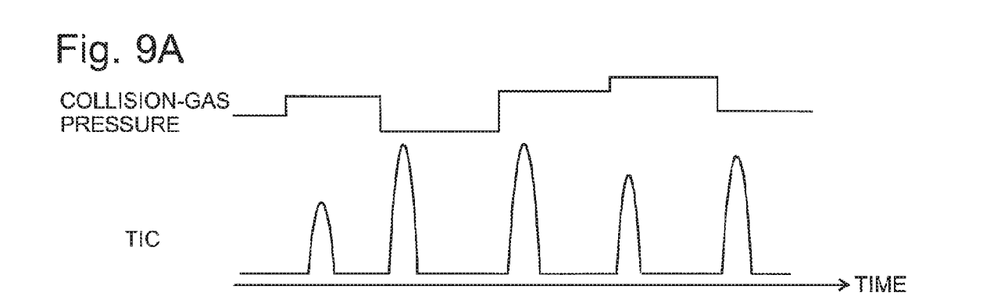
FIGS. 9A and 9B show examples of the relationship between the chromatogram and the change in the collision-gas pressure during a simultaneous multicomponent analysis in the liquid chromatograph triple quadrupole mass spectrometer of the present embodiment.
Figure 9B:
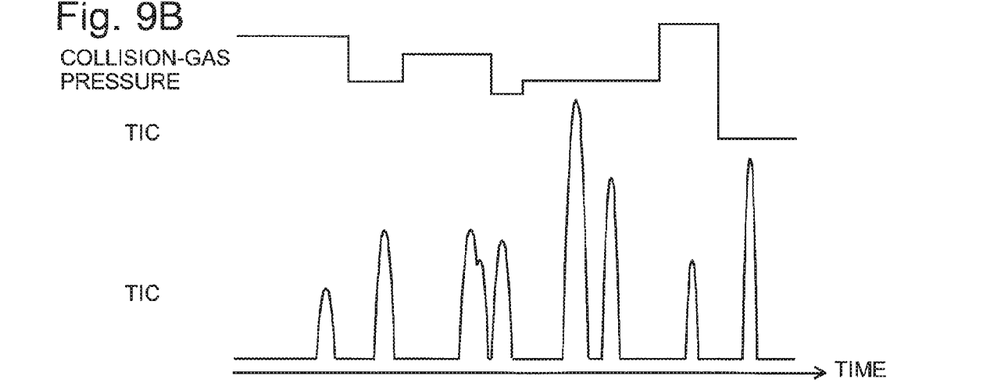

After the actual measurement is initiated in response to a command by the analysis operator (or to other signals), the control unit 41 conducts the measurement while controlling the gas supplier 35 and other elements according to the control sequence stored in the control sequence storage section 45. As a result, the collision-gas pressure in the collision cell 31 changes with the passage of time, for example, as shown in FIG. 9A or 9B. This change corresponds to the compounds sequentially introduced into the mass spectrometer 20 after being temporally separated by the liquid chromatograph 10; for each compound, the collision-gas pressure is set so that the dissociation of the ions originating from that compound occurs with the highest or nearly highest level of efficiency. Consequently, the product ions derived from any of those compounds will be detected with high levels of sensitivity, so that, for example, the area value of a peak on a product ion mass chromatogram created in the data processing unit 40 will be more accurate.

The previous embodiment is an example in which the present invention is applied in an LC/MS/MS. It is evident that the present invention can also be applied in a GC/MS/MS.

Furthermore, any other change, addition or modification appropriately made within the spirit of the present invention will evidently fall within the scope of claims of the present application.

REFERENCE SIGNS LIST

10 . . . Liquid Chromatograph Unit
11 . . . Mobile-Phase Container
12 . . . Liquid-Sending Pump
13 . . . Injector
14 . . . Column
15 . . . Syringe Pump
20 . . . Mass Spectrometer
21 . . . Ionization Chamber
22, 23 . . . Intermediate Chamber
24 . . . Analysis Chamber
25 . . . ESI Probe
26 . . . Heated Capillary
27, 29 . . . Ion Guide
28 . . . Skimmer
30 . . . Front Quadrupole Mass Filter
31 . . . Collision Cell
32 . . . Multipole Ion Guide
33 . . . Rear Quadrupole Mass Filter
34 . . . Ion Detector
35 . . . Gas Supplier
36 . . . Power Source
40 . . . Data Processing Unit
41 . . . Control Unit
42 . . . Optimum Gas Pressure Search Controller
43 . . . Compound-Related Information Storage Section
44 . . . Control Sequence Determiner
45 . . . Control Sequence Storage Section
47 . . . Input Unit
48 . . . Display Unit

The invention claimed is:

1. A chromatograph mass spectrometer including a chromatograph for separating compounds in a sample and a mass analyzer for making an ion having a specific mass-to-charge ratio among ions originating from a compound in a sample separated by the chromatograph undergo a dissociation by a collision with collision gas within a collision cell and for detecting a product ion produced by the dissociation, the chromatograph mass spectrometer comprising:
   a) a gas supplier for supplying the collision gas to the collision cell;
   b) a compound information storage section for storing retention time information and optimum collision-gas pressure information for each compound; and
   c) an analysis controller for retrieving the retention time information and the optimum collision-gas pressure information for a target compound designated as a measurement target from the compound information storage section, and for controlling the gas supplier based on the retrieved information so as to regulate a collision-gas pressure according to a timing at which the target compound is introduced from the chromatograph into the mass analyzer.

2. The chromatograph mass spectrometer according to claim 1, wherein the analysis controller comprises:
   c1) an analysis condition determiner for retrieving, in advance of an execution of a measurement, the retention time information and the optimum collision-gas pressure information for a target compound designated as a measurement target from the compound information storage section, and for determining, based on the retrieved information, analysis condition information showing a change in the collision-gas pressure with respect to a lapse of time in the measurement; and
   c2) a control executer for controlling the gas supplier according to the analysis condition information when the measurement is executed.

3. The chromatograph mass spectrometer according to claim 1, wherein:
   when there are a plurality of target compounds whose elution times overlap each other, the analysis controller designates an arithmetic mean or geometric mean of the optimum collision-gas pressures respectively corresponding to the target compounds as the optimum collision-gas pressure for the elution time where the plurality of target compounds overlap each other.

4. The chromatograph mass spectrometer according to claim 1, wherein:
   the compound information storage section includes information showing a relationship between the collision-gas pressure and a signal strength for each compound; and
   when there are a plurality of target compounds whose elution times overlap each other, the analysis controller designates, as the optimum collision-gas pressure for the elution time where the plurality of target compounds overlap each other, a gas pressure corresponding to an intersection of curves which respectively show the relationship between the collision-gas pressure and the signal strength for the plurality of target compounds.

5. The chromatograph mass spectrometer according to claim 1, wherein:
   the compound information storage section includes information showing a relationship between the collision-gas pressure and a signal strength for each compound; and
   when there are three or more target compounds whose elution times overlap each other, the analysis controller determines the optimum collision-gas pressure for the elution time where the three or more target compounds overlap each other using curves which respectively show the relationship between the collision-gas pressure and the signal strength for two target compounds having a largest difference in the optimum collision-gas pressure among the three or more target compounds.

6. The chromatograph mass spectrometer according to claim 1, wherein:
   the compound information storage section includes information showing a relationship between the collision-gas pressure and a signal strength for each compound; and when there are a plurality of target compounds whose elution times overlap each other, the analysis controller calculates both an arithmetic mean of the optimum collision-gas pressures respectively corresponding to the plurality of target compounds and a geometric mean of the optimum collision-gas pressures respectively corresponding to the plurality of target compounds as candidates of the optimum collision-gas pressure for the elution time where the plurality of target compounds overlap each other, determines another candidate of the optimum collision-gas pressure for the elution time where the plurality of target compounds overlap each other using curves which respectively show the relationship between the collision-gas pressure and the signal strength for the plurality of target compounds, and selects, as the optimum collision-gas pressure for the elution time where the plurality of target compounds overlap each other, the candidate of the optimum collision-gas pressure which causes a smallest amount of decrease in the signal strength for the plurality of target compounds among the candidates of the optimum collision-gas pressure.

7. The chromatograph mass spectrometer according to claim 1, further comprising:
a selection instructor for allowing an analysis operator to select which of the automatically determined collision-gas pressure and a collision-gas pressure entered by the analysis operator should be designated as the optimum collision-gas pressure for the elution time where the plurality of target compounds overlap each other when there are a plurality of target compounds whose elution times overlap each other.

8. The chromatograph mass spectrometer according to claim 7, wherein:
only when the signal strength of at least one of the plurality of target compounds whose elution times overlap each other falls outside a predetermined range from a highest signal strength of that compound under the automatically determined collision-gas pressure, the selection instructor allows the analysis operator to select which of the automatically determined collision-gas pressure and the collision-gas pressure entered by the analysis operator should be designated as the optimum collision-gas pressure for the elution time where the plurality of target compounds overlap each other.

9. The chromatograph mass spectrometer according to claim 8, further comprising:
a display processor for displaying, on a screen of a display unit, a graph showing the relationship between the collision-gas pressure and the signal strength for a plurality of target compounds whose elution times overlap each other.

10. The chromatograph mass spectrometer according to claim 9, further comprising:
a gas pressure indicator for allowing the analysis operator to specify a collision-gas pressure on the graph displayed on the screen of the display unit,
wherein:
the display processor displays the signal strengths of the plurality of target compounds whose elution times overlap each other under the collision-gas pressure specified by the gas pressure indicator.

11. The chromatograph mass spectrometer according to claim 1, further comprising:
a preliminary measurement executer for changing the collision-gas pressure by the gas supplier in a continuous or stepwise manner, with a sample containing a same compound introduced in the mass analyzer, and for acquiring the signal strength of a product ion originating from the compound for every change in the collision-gas pressure; and
an optimum gas pressure extractor for determining the collision-gas pressure at which a peak value of the signal strength is maximized, based on a change in the signal strength corresponding to the change in the collision-gas pressure obtained by the preliminary measurement executer,
wherein:
the collision-gas pressure determined by the optimum gas pressure extractor is used as the optimum collision-gas pressure information to be stored in the compound information storage section.

12. A chromatograph mass spectrometer including a chromatograph for separating compounds in a sample and a mass analyzer for making an ion having a specific mass-to-charge ratio among ions originating from a compound in a sample separated by the chromatograph undergo a dissociation by a collision with collision gas within a collision cell and for detecting a product ion produced by the dissociation, the chromatograph mass spectrometer comprising:
a) a gas supplier for supplying the collision gas to the collision cell;
b) a preliminary measurement executer for changing a collision-gas pressure by the gas supplier in a continuous or stepwise manner, with a sample containing a same compound introduced in the mass analyzer, and for acquiring a signal strength of a product ion originating from the compound for every change in the collision-gas pressure;
c) an optimum gas pressure extractor for determining the collision-gas pressure at which a peak value of the signal strength is maximized, based on a change in the signal strength corresponding to a change in the collision-gas pressure obtained by the preliminary measurement executer; and
d) an analysis controller for controlling the gas supplier, using the optimum collision-gas pressure obtained by the optimum gas pressure extractor, so as to regulate the collision-gas pressure in a measurement in which a sample containing the compound is introduced into the chromatograph, at least when the compound is introduced from the chromatograph into the mass analyzer.

* * * * *